United States Patent [19]

Kagen et al.

[11] Patent Number: 5,236,834
[45] Date of Patent: Aug. 17, 1993

[54] ALLERGENIC MOLECULES FROM LEPIDOGLYPHUS DESTRUCTOR

[76] Inventors: Steven L. Kagen, 100 W. Lawrence St., Appleton, Wis. 54911; Ramasamy Muthiah, 2141 N. Whitney Dr., Appleton, Wis. 54914

[21] Appl. No.: 827,684

[22] Filed: Jan. 30, 1992

[51] Int. Cl.$^5$ .......................... C12Q 1/68; C12Q 1/00; C12P 21/06; G01N 33/53
[52] U.S. Cl. .................... 435/172.1; 435/6; 435/69.3; 435/69.1; 435/7.21; 435/172.3; 436/513; 935/1; 935/2; 935/3; 935/4; 935/9; 935/12
[58] Field of Search ................ 435/69.3, 69.1, 6, 7.21, 435/172.1, 172.3; 536/27; 935/1, 2, 3, 4, 9, 12; 436/513

[56] References Cited

PUBLICATIONS

Old et al (1981) "Principles of Gene Manipulation" U of CA Press, Berkeley, pp. 88-92.
Lathe (1985) Synthetic oligonucleotide probes—J Mol Biol 183:1-12.
Johansson et al (1988) Demonstration of Allergen—Int Archs Allerg Appl. Immunol 85:8-13.
Sambrook et al (1989) "Molecular Cloning" Cold Spring Harbor Press, N.Y., pp. 7.79-7.82.
Freeman et al (1990) Molecular analysis—Plant Mol. Biol 14:297-311.
Ansotegui et al (1991) Identification of a new—Immunol Lett. 27:127-130.
Muthiah et al (1991) Barn Allergy—Abstract 749, J Allergy Clin Immunol 87:326.
Johansson et al (1991) Immunoblot multi-allergen inhibits—Clin Exp Allergy 21:511-518.
Ventas, P., et al., "Identification of IgE-Binding Proteins from Lepidoglyphus destructor and Production of Monoclonal Antibodies to a Major Allergen." 29 Immunology Letters 229-234 (1991).

Primary Examiner—Christine M. Nucker
Assistant Examiner—David R. Preston
Attorney, Agent, or Firm—Quarles & Brady

[57] ABSTRACT

An allergenic protein has been identified from the storage mite *Lepidoglyphus destructor*. A partial amino terminal sequence of the 18 kilodalton protein is presented. Based on this sequence, isolation and cloning of the gene for the allergen becomes possible.

5 Claims, 1 Drawing Sheet

ALLERGENIC MOLECULES FROM LEPIDOGLYPHUS DESTRUCTOR

FIELD OF THE INVENTION

The present invention relates to allergenic diagnosis and therapy in general, and relates, in particular, to the isolation of allergenic proteins and the genes coding for those proteins for use in such diagnosis and therapy.

BACKGROUND OF THE INVENTION

Clinical allergenic responses in humans are typically caused by inappropriate allergic reactivity in susceptible individuals to allergens commonly present in the environment. One class of allergens originates from the detritus of living organisms with which human beings share their environment. One source of such organic allergenic material is arthropods which comprise, of course, most of the animal species existent on the planet. Small arthropods such as insects, arachnids, and crustaceans, are the most important worldwide source of inhalant allergenic organic materials which are capable of causing clinical allergic disorders in susceptible humans. The detritus from these animals is ubiquitous, due to the wide dispersion and high populations of these organisms throughout the human environment. Susceptible humans suffer from allergic conjunctivitis as a result of sensitization and allergic antibody reactivity to these arthropod proteins prevalent in the environment.

The diagnosis and treatment of allergic disease caused by environmental exposure requires both a diagnosis method to determine the source of origin of the allergen, and then treatment to the patient specifically targeted toward the allergen which the patient has heightened sensitivity. Typically diagnosis is done by exposing symptomatic patients to minute quantities of specific allergens and determining which of the allergens elicits allergenic response, such tests often being done by means of "skin prick" tests, or other tests involving small amounts of relatively pure allergen. Once the source of the allergen is identified which causes allergic symptoms in a particular individual, then a therapeutic injection regimen is often indicated which is intended to desensitize the individual to the specific allergen. This may involve injections into the patient of increasing quantities of relatively pure allergen so that circulating levels of antibodies are created to the specific antigen, which has the effect of desensitizing the allergenic reaction in mucosal tissues to the specific allergen. Thus, both for purposes of diagnosis and for therapeutic treatment of allergic disease, the ability to produce quantities of relatively pure allergenic material is highly useful.

Before quantities of allergenic material can be developed for diagnosis or therapeutic uses, the source of the allergenic disease must be defined, both at the organic level and at the molecular level. One class of allergic disease is experienced by farm workers who are known to experience allergic inflammatory airway disease symptoms when exposed to barn dusts. In addition to inflammatory airways disease, other susceptible patients have experienced asthma and dermatitis exposed to such dusts. As early as 1924, Storm van Leeuwen published a report indicating that the storage mites *Acarus siro* and *Lepidoglyphus destructor* were responsible for allergenic asthmatic responses in such patients. Z. Immunf. Exp. Ther., 40:552-569 (1924). Storage mites refer to several species of insects which are often prevalent in stored food materials. Several other mites have been previously proven to be the sources of clinically significant allergenic proteins. Kagen (Ed) "Inhalant Allergy to Arthropods" in *Clinical Review of Allergy*, 8:1-125 (1990). However, the treatment and alleviation of symptoms caused by such storage mites is dependent upon first identifying the allergenic molecules from such organisms, and then either isolating significant quantities of the proteins from such organisms or making available techniques for production of allergenic proteins in heterologous hosts.

SUMMARY OF THE INVENTION

The present invention is summarized in that a method for isolating a gene coding for an allergenic protein from *Lepidoglyphus destructor* includes the steps of constructing at least one nucleotide molecule corresponding to a coding region for at least part of the amino acid sequence of Sequence ID NO. 1 below, and using the nucleotide molecule to recover a coding sequence of a allergenic protein from *Lepidoglyphus destructor*.

It is an object of present invention to enable the creation of the allergenic protein from *Lepidoglyphus destructor* in heterologous hosts by enabling the cloning of the gene coding for that protein.

It is another object of the present invention to enable the production of allergenic proteins from *L. destructor* for use in the diagnosis and therapeutic treatment of allergenic disease attributable to this organism.

Other objects, advantages, and features from the present invention will become apparent from the following specification.

DETAILED DESCRIPTION OF THE INVENTION

Figure 1:
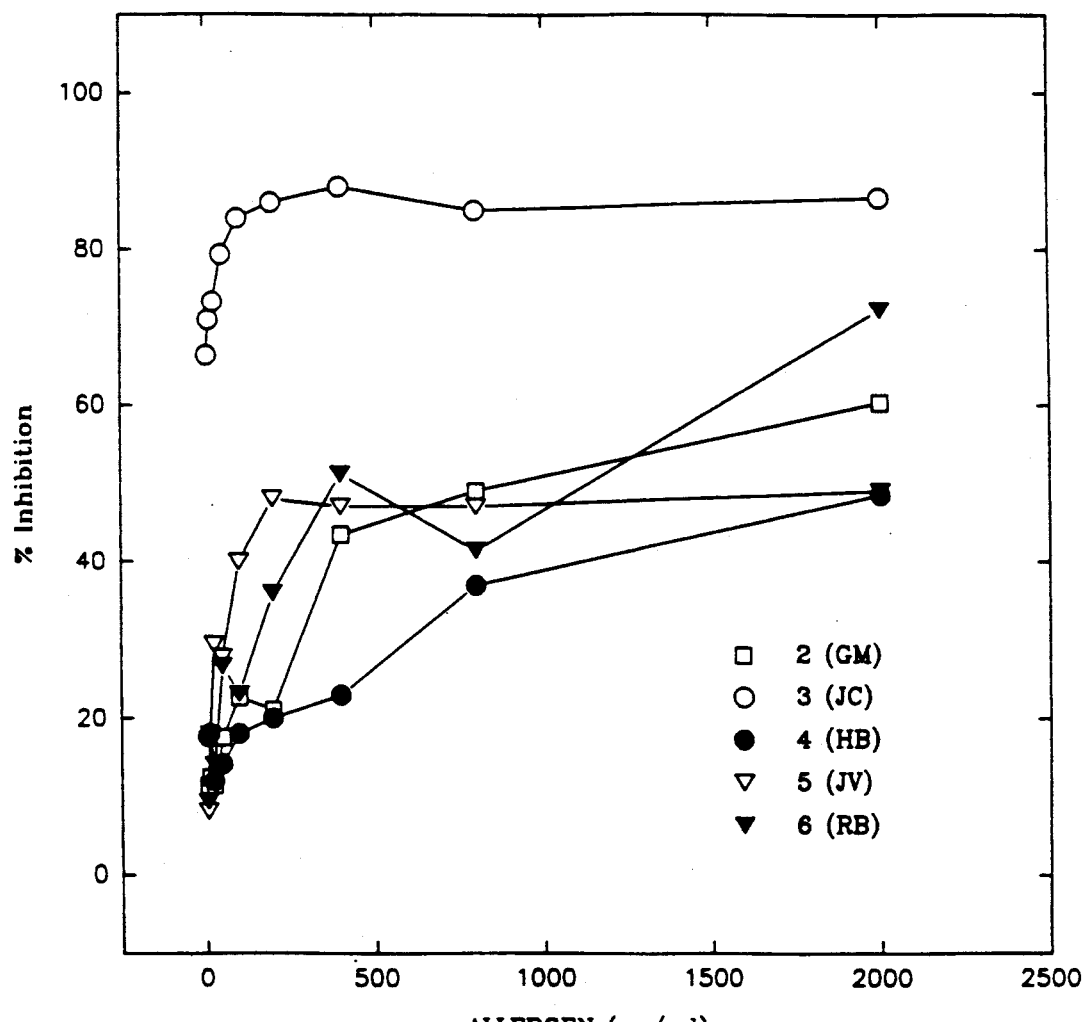
FIG. 1 is a graphical representation of a competitive ELISA binding assay conducted in the process of identifying the allergenic molecule of the present invention.

The present invention is directed toward the isolation of a specific 18 kilodalton allergenic protein from *Lepidoglyphus destructor*. Not only has an allergenic molecule responsible for allergic symptoms been identified, a partial amino acid sequence for the protein has been elucidated which is sufficient to enable the cloning of the gene for the allergen so that the allergenic protein can now be produced in heterologous host systems. Various immunological techniques have been used to identify the specific allergen and have confirmed the allergenicity of the protein. The protein has been found to be unique, and is not cross-reactive to allergenic extracts for other storage mites or house dust mite antigens which are known.

The function of the allergenic molecule in the storage mite is unknown. It is known that the allergenic protein is present in the detritus left by the animal.

The allergenic protein which has been identified from *L. destructor* has been identified using comparative sera analysis from rural patients experiencing allergic disease symptoms attributable to barn dust. Various immunological techniques, largely based on enzyme linked immunoassay (ELISA) and electrophoretic and blotting techniques, have been used to identify the allergenic proteins from extracts of the insect itself. Based on this data, two potentially allergenic proteins were identified on electrophoresis gels which co-migrated with allergenic activity and reactivity with the sera of susceptible patients. The two allergenic proteins were identified to be approximately 18 and 21 kilodaltons in size respectively. Neither of the proteins was reactive to antisera to other storage mite or house dust mite allergenic extracts. A partial amino terminal sequencing of the 18 kilodalton allergen has revealed the amino acid sequence presented as Sequence ID No: 1 below. Although the amino terminal sequencing of the protein is clearly not complete, sufficient sequence is available for many purposes. First, the existence of a defined 10 amino acid sequence, beginning with amino acid number 11, allows for oligonucleotides of up to 30 bases in length to be created. Such oligonucleotides can be used as probes in the process of isolating the entire coding sequence for the protein. Such probes can be used in a DNA hybridization technique to recover an mRNA strand from extracts of whole mRNA produced by the insect. Such differential hybridization, and isolation of the appropriate mRNA for this protein, then allows a cDNA to be created to the mRNA using conventional molecular biology techniques. It is well known that such cDNA sequences can be incorporated into vectors for expression in heterologous hosts. This is done by attaching the appropriate promoter and transcription termination regions to the cDNA so as to produce a vector which will express the cDNA in appropriate hosts to produce the desired allergenic protein. Although such coding sequences can be produced in a wide variety of heterologous host organism systems, it would be particularly appropriate that a gene such as this one be expressed in insect cell expression systems, several of which are known and commercially available to those of ordinary skill in the art, in order that correct glycosylation of the protein be achieved to insure antigenic response identical to that provided by the allergen from the native host. Other techniques for isolating genes from amino acid sequences are also known, such as those based on the polymerase chain reaction (PCR), and other amplification techniques, which rely more on amplifying the gene sequence from the native DNA. In any event, one of ordinary skill in the art armed with the partial amino acid sequence is capable of recovering the DNA sequence coding for the native protein from the storage mite, and once that sequence is recovered, it becomes a matter well within the ordinary skill of the art to produce the protein in other heterologous hosts.

EXAMPLES

To commence the investigation of the allergenic molecules present in *L. destructor*, samples of storage mites propagated in culture were necessary. Pure cultured storage mites of species *A. siro*, *L. destructor*, and *T. putricentiae* were obtained in freeze dried form from an academic colleague (F. Spieksman, Leiden, The Netherlands). Previously, allergenic extracts have been created for other storage mites and the allergenic extracts of *D. pteronyssinus* and *D. farinae* were obtained from commercial sources (H. Stier). Monoclonal antibodies to these specific two allergenic extracts were also obtained from a colleague. Patients complaining of allergenic symptoms associated with barn dust who were receiving clinical treatment consented to donate sera to be used in the appropriate allergenic cross-reactivity experiments described below.

First, crude extracts prepared from *L. destructor* were resolved on Western blot analysis, by molecular size, and then incubated with sera from allergenic patients. After washing, the blots were probed with radiolabeled goat anti-human IgE to locate the location of binding of the anti-human antibodies to the gels. Coomassie blue staining of the SDS-page gels thus created revealed two protein bands which reacted with the sera from the patients, one at 18 kilodaltons and one at 21 kilodaltons. Once the bands were found to be within this range, it became relatively easy to size fractionate the total protein recovered from disrupted *L. destructor* cultures, and use the size isolated proteins as crude extracts of the *L. destructor* allergen.

It then became possible to compare the allergenic response of susceptible patients to the *L. destructor* allergen/antigen, as compared to other antigenic molecules available for other storage mites. A ELISA assay test was conducted using allergenic extracts from *D. farinae, L. destructor, T. putricentiae* and *A. siro.* The response associated with a normal patient exhibiting no clinical allergenic symptoms to any of these organisms was arbitrarily set as a standard. Against that standard, the sera of five symptomatic patients was compared to determine the specific IgE binding to each of the four antigens. The results are presented in Table 1 below. As may be seen by that table, certain patients had extraordinarily high reactivity to the *L. destructor* antigen, while others were more responsive to other of the antigens. It would appear that all the individuals were responsive at elevated levels to the antigens and that the pattern of allergenic response to the antigens varied from individual to individual.

TABLE I

| | MITE ALLERGEN SPECIFIC IgE BINDING | | | |
|---|---|---|---|---|
| PATIENT | D. FARINAE | L. DESTRUCTOR | T. PUTRICENTIAE | L. SIRO |
| 1. Normal | 100 | 100 | 100 | 100 |
| 2. GM | 102 | 320 | 178 | 132 |
| 3. JC | 138 | 518 | 330 | 135 |
| 4. HB | 190 | 410 | 414 | 163 |
| 5. JV | 593 | 153 | 138 | 177 |
| 6. RB | 350 | 206 | 200 | 234 |

Although this data seemed to strongly indicate that the allergenic molecule in *L. destructor* was distinct from those allergens from the other storage mites which had been previously identified, it was decided to verify this to the extent possible using the available monoclonal antibodies. Thus allergenic analysis was undertaken using the available monoclonal antibodies, designated MAB.Der pl and MAB.Der fl. These monoclonal antibodies were used to probe the allergen samples from *D. farinae, D. pteronyssinus,* and *L. destructor. The results are presented in Table* 2 below. As may be seen by reference to that table, the antibodies had specific affinity for the antigens to which they were intended, but neither reacted measurably against the isolated antigen from *L. destructor.*

TABLE II
ALLERGEN ANALYSIS USING MONOCLONAL ANTIBODIES

| ALLERGEN SAMPLE | MAB. Der pI SPECIFIC ALLERGEN | MAB. Der fI SPECIFIC ALLERGEN |
| --- | --- | --- |
| D. Farinae | 9940 ng/ml | 64560 ng/ml |
| D. Pteronyssinus | 17280 ng/ml | 00 |
| L. Destructor | 00 | 00 |

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
    (A) LENGTH: 29 amino acids
    (B) TYPE: amino acid
    (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
    (A) ORGANISM: Lepidoglyphus destructor (xi) SEQUENCE DESCRIPTION: SEQ ID NO:1:

```
Xaa Lys Met Thr Xaa Xaa Xaa Xaa Xaa Xaa Gly Glu Val Thr Glu Leu
 1               5                       10                  15

Asp Ile Thr Gly Xaa Xaa Gly Asp Thr Xaa Val Ile Xaa
                 20                  25
```

The 18 kilodalton allergen was prepared in quantity, isolated by size fractionation, and then supplied for protein sequencing. The sequencing was performed using an applied biosystems model 477A pulsed liquid phase sequencer with an on-line phenylthiohydantonin amino acid analysis performed by an ABI Model 120A analyzer from the Western Blot. The sequence obtained from the automated sequence analysis was Sequence ID No. 1 below.

Comparison of this partial amino acid sequence with available mite allergen amino acid sequence data contained within available data banks further reinforced the conclusion that this $L.$ destructor allergen was unique among storage mite antigens.

ELISA inhibition studies were done using conventional techniques with sera from susceptible patients, to determine the binding inhibition created by the putative $L.$ destructor extracts on $L.$ destructor binding to IgE from susceptible patients. FIG. 1 illustrates graphically the results of this analysis, with the percent of inhibition plotted against the density of the allergen. Analysis of the results shows that using the $D.$ farinae allergen to inhibit the binding between the $L.$ destructor antigen and IgE from the same susceptible patients revealed negligible inhibition at all.

The availability of the partial amino acid sequence presented in Sequence ID No. 1 below will enable the cloning of the gene coding for the production of this protein in the $L.$ destructor to be isolated and cloned. The partial amino acid sequence presented below contained sufficient amino acid information that, even considering the degenerate nature of the relationships between nucleotides and amino acids, that oligonucleotides can be prepared sufficient to probe for mRNA of this protein found within mRNA extracts from cultures of the organism. Using such identified mRNA, cDNA clones can be created so as to readily provide copies of the protein coding sequence which can be inserted into heterologous hosts for production of this allergenic molecule.

We claim:

1. A method of isolating a gene coding for an 18 and 21 kilodalton allergenic protein from *Lepidoglyphus destructor* comprising the steps of
   constructing at least one nucleotide molecule corresponding to a DNA coding region corresponding to at least a part of the amino acid sequence of SEQ:ID:NO:1, and
   using the constructed nucleotide molecule to recover a complete coding sequence for the 18 and 21 kilodalton allergenic protein from *Lepidoglyphus destructor*.

2. A method as claimed in claim 1 wherein the constructed nucleotide molecule is a DNA sequence comprising codons for at least 5 sequential of the amino acids from amino acid number 11 to amino acid number 20 of SEQ:ID:NO:1.

3. A method as claimed in claim 1 wherein the step of using the constructed nucleotide molecule to recover a complete coding sequence is performed by using the constructed nucleotide molecule to recover an mRNA molecule and constructing a cDNA molecule complementary to the mRNA molecule.

4. A DNA molecule coding for an 18 and 21 kilodalton allergenic protein from *Lepidoglyphus destructor* isolated from its host by the method of claim 1.

5. An isolated DNA sequence coding for an 18 and 21 kilodalton allergenic protein from *Lepidoglyphus destructor* comprising the amino acid sequence of SEQ:ID:NO:1.

* * * * *